United States Patent [19]
Yavitz

[11] Patent Number: 6,009,876
[45] Date of Patent: Jan. 4, 2000

[54] METHOD FOR MODIFYING AND RESHAPING COLLAGEN BENEATH THE SURFACE OF SKIN

[76] Inventor: Edward Q. Yavitz, 3828 Spring Creek Rd., Rockford, Ill. 61114

[21] Appl. No.: 08/858,967

[22] Filed: May 20, 1997

[51] Int. Cl.[7] .................................................. A61B 19/00
[52] U.S. Cl. ............................................. 128/898; 606/9
[58] Field of Search ................................ 606/2, 3, 9–19; 128/898; 607/89, 94, 88, 90

[56] References Cited

U.S. PATENT DOCUMENTS

| | | |
|---|---|---|
| 3,074,407 | 1/1963 | Moon et al. . |
| 4,156,124 | 5/1979 | Macken et al. . |
| 4,461,285 | 7/1984 | Villasenor et al. . |
| 4,461,294 | 7/1984 | Baron . |
| 4,840,175 | 6/1989 | Peyman . |
| 4,903,695 | 2/1990 | Warner et al. . |
| 4,905,711 | 3/1990 | Bennet et al. . |
| 4,976,709 | 12/1990 | Sand . |
| 5,057,104 | 10/1991 | Chess . |
| 5,092,863 | 3/1992 | Schanzlin . |
| 5,108,412 | 4/1992 | Krumeich et al. . |
| 5,137,530 | 8/1992 | Sand . |
| 5,282,797 | 2/1994 | Chess . |
| 5,312,395 | 5/1994 | Tan et al. ...................................... 606/9 |
| 5,336,215 | 8/1994 | Hsueh et al. . |
| 5,356,409 | 10/1994 | Nizzola . |
| 5,437,657 | 8/1995 | Epstein . |
| 5,486,172 | 1/1996 | Chess . |
| 5,582,608 | 12/1996 | Brown . |
| 5,611,795 | 3/1997 | Slatkine et al. . |
| 5,616,139 | 4/1997 | Okamoto . |
| 5,649,922 | 7/1997 | Yavitz . |

FOREIGN PATENT DOCUMENTS

| | | |
|---|---|---|
| 0531756 | 3/1993 | European Pat. Off. . |
| WO 92/01430 | 2/1992 | WIPO . |
| 92/10152 | 6/1992 | WIPO . |
| 94/18920 | 9/1994 | WIPO . |
| WO 95/15134 | 6/1995 | WIPO . |

Primary Examiner—Mickey Yu
Assistant Examiner—Kelly O'Hara
Attorney, Agent, or Firm—Fletcher, Yoder & Van Someren

[57] ABSTRACT

A cosmetic system and technique are provided for improving the texture and appearance of an individual's skin. The system includes an energy absorption modifier that may be applied to a portion of the individual's epidermis. The energy absorption modifier is designed to displace water within that portion. Energy from an appropriate laser or infrared lamp can then be directed to a treatment area beneath the epidermal layer without detrimental heat buildup in that area of the epidermis.

17 Claims, 1 Drawing Sheet

METHOD FOR MODIFYING AND RESHAPING COLLAGEN BENEATH THE SURFACE OF SKIN

FIELD OF THE INVENTION

The present invention relates generally to a cosmetic system and method for improving the appearance of skin, and particularly to the use of an energy source that stimulates tissue beneath the epidermis of an individual without damaging the epidermis.

BACKGROUND OF THE INVENTION

Heat has long been used to modify and reshape collagen beneath the surface of the skin. Egyptians used salt, oil and alabaster to improve skin texture and Turks used fire to singe the surface of the skin. In the twentieth century, chemical peels implementing phenol and trichloacetic acid were introduced to reduce wrinkles and remove other anomalies of the skin. Lasers, such as carbon dioxide lasers, were also developed and used for the reduction or elimination of wrinkles, such as periorbital wrinkles, and other anomalies of the skin.

Such methods were more or less effective in reducing or eliminating wrinkles by providing energy in the form of heat to the subepidermal layer between the epidermis and the dermis of an individual's skin. Heat stimulates release of factors that promote new collagen growth and a thicker healthier matrix of elastins and collagen to provide a younger looking skin. However, these techniques result in removal, destruction or damage to the epidermis proximate the area in which heat is applied to the subepidermal layer. The damage or destruction of the epidermis results in redness, loss of body fluid and a greater potential for infection.

For example, with lasers, laser light energy is used to heat tissue beneath the epidermis, but the laser light energy must pass through the epidermis on its way to the treatment area. This laser light energy is absorbed by the epidermis as it passes therethrough and generates unwanted heat that effectively ablates the epidermal layer in the area of treatment. After time, the epidermis heals and grows back over the treatment area.

Attempts have been made to minimize injury to the epidermis by removing heat from the epidermal area proximate the area of treatment. This is typically accomplished by delivering a coolant to the epidermis at the area where it is penetrated by the laser beam. However, this adds to the complexity of the equipment and the procedure.

It would be advantageous to have an energy absorption modifier that could be applied to the epidermis to permit the transfer of certain types of electromagnetic energy through the epidermis to the area of treatment without absorption of energy and the resultant detrimental buildup of heat in that area of the epidermis.

SUMMARY OF THE INVENTION

The present invention features a cosmetic method for improving the appearance of the skin of an individual. The method comprises the steps of applying an energy absorption modifier to a portion of the epidermis of the individual. The method further includes directing energy through the portion of the epidermis of the individual and heating a desired area of the subepidermis of the individual. The heating is accomplished via absorption of energy at the desired area without causing detrimental heat buildup in the portion of the epidermis.

According to another aspect of the invention, a method is provided for using a light emitter to stimulate new collagen growth within tissue disposed beneath the epidermis of an individual without damaging the epidermis. The method comprises the steps of orienting a light emitter to direct light energy through a portion of the epidermis of an individual. The portion of the epidermis is treated with an energy absorption modifier which displaces water (hereinafter water means $H_2O$) within the portion. The method further comprises the step of directing the light energy toward the portion of the epidermis for an adequate period of time to cause sufficient heating for the promotion of new collagen growth in a desired region of tissue beneath the epidermis.

According to another aspect of the invention, a composition is provided for application to the epidermis of an individual to reduce the absorption of certain types of electromagnetic energy that strike the epidermis. The composition comprises an energy absorption modifier that may be applied to a portion of the epidermis of an individual. The energy absorption modifier is formulated to displace water within the portion of the epidermis, and preferably comprises one of either deuterium oxide or tritium oxide.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

The present invention includes a system and method by which the outermost layer of a body can be protected while internal tissues are altered, typically by heating. The following discussion will focus on protection of the epidermis during treatment of underlying tissue, but this system and method can also be used on other external layers of the body, such as the epithelium of the eye.

Figure 1:
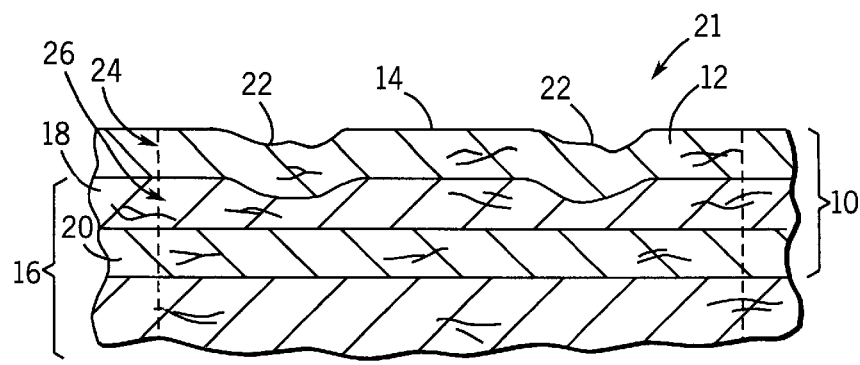
FIG. 1 is a cross-sectional view of a portion of an individual's skin.

Referring generally to FIG. 1, a cross-section of a portion of human skin 10 is illustrated. The skin includes an outer epidermal layer or epidermis 12 having an outer surface 14. Outer surface 14 is the visible surface of an individual's skin.

Additional tissue 16 is disposed beneath epidermis 12 and includes layers of skin 10 as well as deeper tissue. For example, skin 10 includes a subepidermal layer 18 disposed between epidermis 12 and a dermal layer or dermis 20.

In FIG. 1, skin 10 is illustrated as having an anomaly 21, such as wrinkles 22, disposed along a portion 24 of epidermis 12. One way of improving the appearance of skin 10, and particularly portion 24 of epidermis 12, is to heat an area of tissue 16 disposed beneath portion 24. In particular, it is desirable to sufficiently heat a desired treatment area 26 of subepidermal layer 18. Heating treatment area 26 tends to shrink wrinkles 12 and stimulate the release of factors that promote new collagen growth and a thicker healthier matrix of elastins and collagen that provide skin 10 with a younger, healthier appearance. This wrinkle reduction effect is also achieved with conventional laser treatment techniques.

Figure 2:
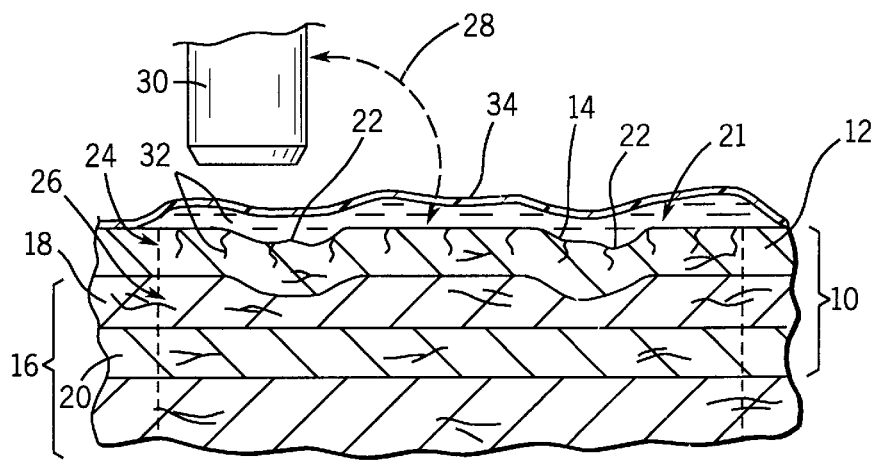
FIG. 2 is a cross-sectional view similar to FIG. 1 but with an energy absorption modifier applied.

Referring now to FIG. 2, a system 28 according to a preferred embodiment of the present invention, is illustrated. System 28 includes an energy emitter 30, an energy absorption modifier 32 and a protectant layer 34 disposed over energy absorption modifier 32 after it is applied to portion 24 of epidermis 12.

Energy emitter 30 preferably emits energy in the form of electromagnetic radiation that can be absorbed by tissue 16, e.g., desired treatment area 26 of subepidermal layer 18, to create heat within that tissue area. In the preferred embodiment, energy emitter 30 is a light emitter, such as a carbon monoxide laser or an Nd:YAG laser having a wavelength of approximately 1320 nanometers. Energy emitter 30 can also be a non-laser light emitter, such as an infrared light emitter and specifically a pulsed infrared lamp.

If a laser light energy emitter is used, it can be mounted on a mechanical carrier or hand-held by a person providing the skin rejuvenation treatment. In either case, the energy emitter 30 is oriented to direct energy through portion 24 of epidermis 12 to the desired treatment area, such as area 26. The energy emitter 30 is moved along outer surface 14 of portion 24 until the area of anomaly 21 has been fully treated and the anomaly, e.g. wrinkles 22, has been reduced or eliminated. Handling and movement of the laser is comparable to the procedures currently employed by those conducting conventional laser treatments.

Potentially, the laser light can be diffused over a greater area, or a large infrared lamp can be used to direct energy toward a relatively large portion of epidermis 12 for absorption by a relatively large desired treatment area 26. In fact, the energy may be provided by multiple infrared lamps distributed through, for example, a tanning bed to promote widespread reinvigoration of skin. Of course, the time of exposure to energy from energy emitter 30 will vary depending on the intensity of the energy and the area over which it is spread.

Energy absorption modifier 32 is a material formulated to cooperate with epidermis 12 to permit light energy, such as laser light from a carbon monoxide or Nd:YAG laser or light from an infrared lamp, to pass through portion 24 of epidermis 12 with reduced or no absorption of the energy by the tissue of epidermis 12. This permits treatment of tissue beneath the epidermis via appropriate lasers or infrared emitters (see FIG. 3) without detrimental heat buildup in portion 24 of epidermis 12. Thus, there is no damage or ablation of portion 24. Additionally, because energy absorption by epidermis 12 is reduced or eliminated, it is not necessary to continuously remove heat from portion 24 via a coolant. This improves the safety and effectiveness of skin rejuvenation with the aid of lasers or other energy emitters designed to stimulate tissue beneath the epidermal layer.

Preferably, energy absorption modifier 32 is formulated to displace the water($H_2O$) within portion 24 when applied to epidermis 12. This water within the epidermal layer absorbs energy from certain lasers or other energy emitters, such as those described above, and results in the damaging heat buildup within epidermis 12. By displacing some or all of the water within portion 24 of epidermis 12, the energy from these types of energy emitters is permitted to pass through the epidermal layer to the subepidermal layer 18 or other tissue beneath epidermis 12. The result is reduced heat buildup in portion 24 of epidermis 12 during the treatment procedure. The epidermis remains intact which lessens the chance of infection, decreases redness and loss of body fluid and substantially shortens the healing time.

Figure 3:
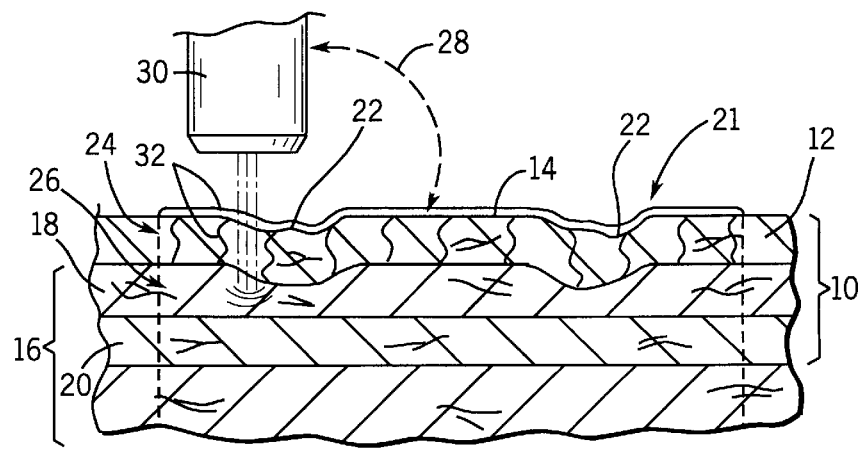
FIG. 3 is a cross-sectional view similar to that of FIG. 2 but also showing a light emitter interacting with the tissue beneath the epidermis.

Energy absorption modifier 32 is typically in liquid form and preferably comprises deuterium oxide. In an alternate embodiment, energy absorption modifier 32 comprises tritium oxide. Both of these chemicals are able to replace the water content of the epidermis or the epithelium of the eye to permit energy to pass through to tissues beneath this outer layer, as best illustrated in FIG. 3.

After energy absorption modifier 32 is applied to portion 24 of epidermis 12, it typically is covered by protectant layer 34. With certain chemicals, such as deuterium oxide or tritium oxide, evaporation occurs relatively rapidly and protectant layer 34 helps prevent this occurrence as energy absorption modifier 32 is absorbed by epidermis 12 to displace the water content in portion 24. Typically, protectant layer 34 is impermeable or semi-permeable to air. For example, protectant layer 34 can be a sheet of plastic applied over energy absorption modifier 32 and epidermis 12. Potentially, energy can be directed through protectant layer 34 toward the desired treatment area 26, but it is preferred that protectant layer 34 be removed prior to stimulating the desired treatment area 26 via energy emitter 30.

In practicing the invention, dead skin cells typically are exfoliated from epidermis 12 along outer surface 14 of portion 24. Dilute glycolic acid, alphahydroxy or citric acid can be used to exfoliate the dead skin. Following exfoliation, energy absorption modifier 32 is applied to portion 24 and covered by protectant layer 34. Energy absorption modifier 32 is provided sufficient time to be absorbed by portion 24, thereby displacing the water normally within that part of the epidermal layer. The protectant layer 34 is then removed and energy emitter 30 is used to direct energy through portion 24 to desired treatment area 26. As with conventional techniques, the energy supplied to desired treatment area 26 must sufficiently heat the area to shrink wrinkles and stimulate the release of factors that promote new collagen growth. After treatment of area 26, the epidermis 12 remains intact and the individual is left with healthier, younger looking skin.

It will be understood that the foregoing description is of preferred exemplary embodiments of this invention and that the invention is not limited to the specific forms shown. For example, a variety of energy emitters may be used, the intensity of the energy and time over which it is directed against the skin of an individual will vary depending on the degree and type of the anomalies, e.g., wrinkles, being treated. Although this system and method may most readily be used to reduce or eliminate wrinkles in various locations of an individual's face, the system and method can be used to modify and reshape collagen beneath the outer surface of the body in other areas, including an individual's eyes. Additionally, the energy absorption modifier can be formulated in several different ways. For example, it can include conventional carrier ingredients such as those found in commonly used lotions or it can be mixed with an exfoliant to permit combination of exfoliation and application of the energy absorption modifier. These and other modifications may be made in the design and arrangement of the elements without departing from the scope of the invention as expressed in the appended claims.

What is claimed is:

1. A cosmetic method for improving the appearance of the skin of an individual, comprising the steps of:

applying an energy absorption modifier to a portion of the epidermis of the individual;

displacing the naturally occurring water in the portion of the epidermis;

directing energy through the portion of the epidermis of the individual; and heating a desired area of the subepidermis of the individual via a greater absorption of the energy in the desired area than in the portion of the epidermis, due to displacement of the naturally occurring water.

2. The cosmetic method as recited in claim 1, wherein the step of applying includes applying an isotopic variant of $H_2O$ that differs from the naturally occurring water in the portion of the epidermis.

3. The cosmetic method as recited in claim 1, further comprising the steps of applying an air impermeable material over the energy absorption modifier;

waiting a predetermined time period; and removing the air impermeable material prior to the step of directing.

4. The cosmetic method as recited in claim 1, wherein the step of directing comprises directing light energy through the portion of the epidermis.

5. The cosmetic method as recited in claim 1, wherein the step of directing comprises directing infrared light energy through the portion of the epidermis.

6. The cosmetic method as recited in claim 1, further comprising the step of exfoliating a collection of dead skin cells from the portion of the epidermis.

7. The cosmetic method as recited in claim 6, wherein the step of directing comprises directing light energy through the portion of the epidermis.

8. The cosmetic method as recited in claim 7, wherein the step of applying includes the step of applying a deuterium oxide to the portion of the epidermis.

9. The cosmetic method as recited in claim 7, wherein the step of applying includes applying an isotopic variant of $H_2O$ that differs from the naturally occurring water in the portion of the epidermis.

10. The cosmetic method as recited in claim 1, wherein directing comprises directing laser energy through the portion of the epidermis.

11. The cosmetic method as recited in claim 1, wherein directing comprises directing energy from a carbon monoxide laser through the portion of the epidermis.

12. A cosmetic method for improving the appearance of the skin of an individual, comprising the steps of:

applying an energy absorption modifier to a portion of the epidermis of the individual;

directing energy through the portion of the epidermis of the individual; and heating a desired area of the subepidermis of the individual via a greater absorption of the energy in the desired area than in the portion of the epidermis, wherein the step of applying includes the step of applying a deuterium oxide to the portion of the epidermis.

13. A cosmetic method for improving the appearance of the skin of an individual, comprising the steps of:

displacing at least a portion of the naturally occurring water in an area of the epidermis of an individual;

directing an energy, normally absorbed by the naturally occurring water, through the area and into a specific region beneath the epidermis; and heating the specific region via greater energy absorption than in the area of the epidermis.

14. The cosmetic method as recited in claim 13, wherein displacing comprises applying an isotopic variant of $H_2O$ that differs from the naturally occurring water in the area of the epidermis.

15. The cosmetic method as recited in claim 13, wherein displacing comprises applying an absorption modifier containing a deuterium oxide.

16. The cosmetic method as recited in claim 13, wherein directing includes directing a laser light energy.

17. The cosmetic method as recited in claim 13, wherein directing includes directing a CO laser light energy.

* * * * *